United States Patent
Fukasawa et al.

(10) Patent No.: US 10,054,685 B2
(45) Date of Patent: Aug. 21, 2018

(54) FOREIGN-MATTER DETECTING APPARATUS AND METHOD FOR DETECTING FOREIGN-MATTER IN POWDER USING TERAHERTZ PULSE WAVE

(71) Applicant: NIPRO CORPORATION, Osaka (JP)

(72) Inventors: Ryoichi Fukasawa, Ohtawara (JP); Shigenori Tominaga, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

(21) Appl. No.: 14/408,392

(22) PCT Filed: Jun. 14, 2013

(86) PCT No.: PCT/JP2013/066479
§ 371 (c)(1),
(2) Date: Dec. 16, 2014

(87) PCT Pub. No.: WO2013/191103
PCT Pub. Date: Dec. 27, 2013

(65) Prior Publication Data
US 2015/0234047 A1 Aug. 20, 2015

(30) Foreign Application Priority Data
Jun. 18, 2012 (JP) .................... 2012-137127

(51) Int. Cl.
G01S 17/02 (2006.01)
(52) U.S. Cl.
CPC .................. G01S 17/026 (2013.01)
(58) Field of Classification Search
CPC .............. G01S 17/026; G01N 21/3581; G01N 21/3563; G01N 21/85; G01N 21/3586;
(Continued)

(56) References Cited

U.S. PATENT DOCUMENTS 6,727,342 B1 * 4/2004 Bastioli .................. C08L 67/02
428/35.1
8,716,666 B1 * 5/2014 Demers et al. .......... 250/339.05
(Continued)

FOREIGN PATENT DOCUMENTS

GB 2486098 6/2012
JP 2001-004549 1/2001
(Continued)

OTHER PUBLICATIONS

International Search Report dated Jul. 23, 2013 in International (PCT) Application No. PCT/JP2013/066479 with English translation.
(Continued)

Primary Examiner — David Porta
Assistant Examiner — Blake Riddick
(74) Attorney, Agent, or Firm — Wenderoth, Lind & Ponack, L.L.P.

(57) ABSTRACT

A foreign matter detecting apparatus includes an oscillating unit, an optical system, a receiving unit, a scanning mechanism, and an operator. The oscillating unit generates a terahertz pulse wave and emits the terahertz pulse wave as irradiation light. The optical system guides the irradiation light to the first part of the container and condenses reflected light from the container. The receiving unit outputs a signal corresponding to the condensed reflected light and also measures an echo. The scanning mechanism scans a position of the irradiation light guided on the first part in a two-dimensional manner. The operator detects foreign matter in powder in a container based on at least one of a time waveform signal, a reflection image, a power spectrum, a tomographic image, and a frequency image. The time waveform signal is output from the receiving unit in chronological order.

10 Claims, 14 Drawing Sheets

(58) Field of Classification Search
CPC .... G01N 21/4795; G01N 21/88; G01N 21/94; G01J 3/42
USPC ..... 250/338.1, 339.06, 341.8, 348, 350, 351
See application file for complete search history.

(56) References Cited

U.S. PATENT DOCUMENTS

| | | | |
|---|---|---|---|
| 2004/0010196 A1* | 1/2004 | Wang et al. | 600/476 |
| 2005/0056785 A1* | 3/2005 | Chou et al. | 250/338.1 |
| 2006/0043298 A1 | 3/2006 | Kawase et al. | |
| 2006/0056586 A1* | 3/2006 | Uetake et al. | 378/57 |
| 2006/0235621 A1 | 10/2006 | Cole et al. | |
| 2008/0123109 A1* | 5/2008 | Iwasaki | G06T 7/0057 356/610 |
| 2010/0148069 A1* | 6/2010 | Ouchi | 250/341.8 |
| 2010/0148070 A1* | 6/2010 | Ho et al. | 250/341.8 |
| 2011/0032601 A1* | 2/2011 | Kondo et al. | 359/330 |
| 2011/0133087 A1* | 6/2011 | Mann | G01V 8/005 250/338.4 |
| 2011/0253897 A1* | 10/2011 | Saeedkia et al. | 250/358.1 |
| 2012/0032083 A1 | 2/2012 | Itsuji | |
| 2012/0050841 A1 | 3/2012 | Okano | |
| 2013/0320216 A1* | 12/2013 | Aiko et al. | 250/349 |

FOREIGN PATENT DOCUMENTS

| | | |
|---|---|---|
| JP | 2001-66375 | 3/2001 |
| JP | 2004-101257 | 4/2004 |
| JP | 2006-71412 | 3/2006 |
| JP | 2006-516722 | 7/2006 |
| JP | 2006-216851 | 8/2006 |
| JP | 2008-151618 | 7/2008 |
| JP | 2010-8139 | 1/2010 |
| JP | 2010-204035 | 9/2010 |
| JP | 2010-216890 | 9/2010 |
| JP | 2011-127959 | 6/2011 |
| JP | 4759770 | 8/2011 |
| JP | 2012-37293 | 2/2012 |
| WO | 2004/063726 | 7/2004 |
| WO | 2008/001785 | 1/2008 |
| WO | 2009/156468 | 12/2009 |
| WO | 2010/119486 | 10/2010 |
| WO | 2010/119646 | 10/2010 |
| WO | 2012/056524 | 5/2012 |
| WO | WO 2012056524 A1 * | 5/2012 |

OTHER PUBLICATIONS

Extended European Search Report dated May 19, 2016 in corresponding European Application No. 13807600.5.

* cited by examiner

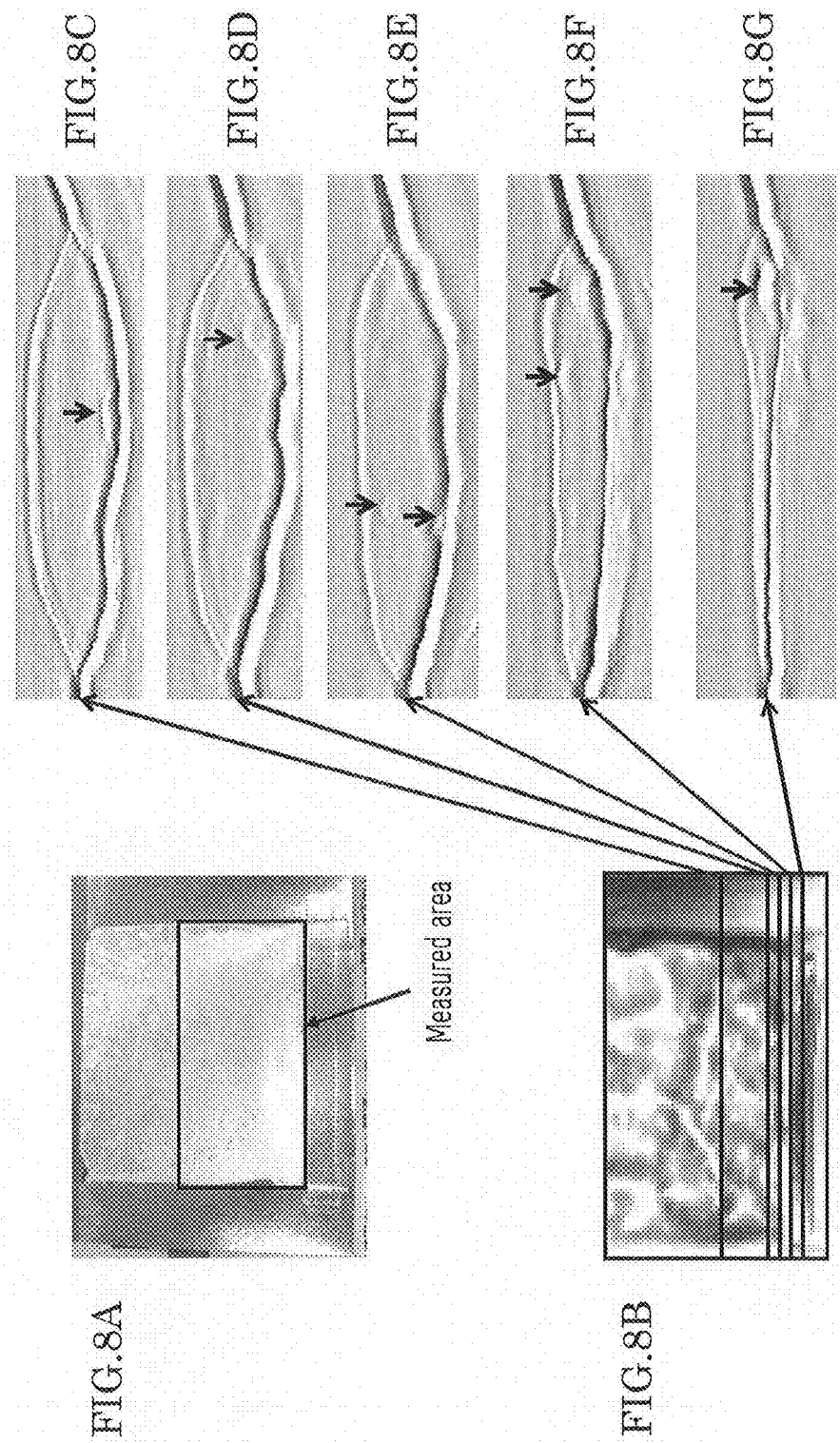

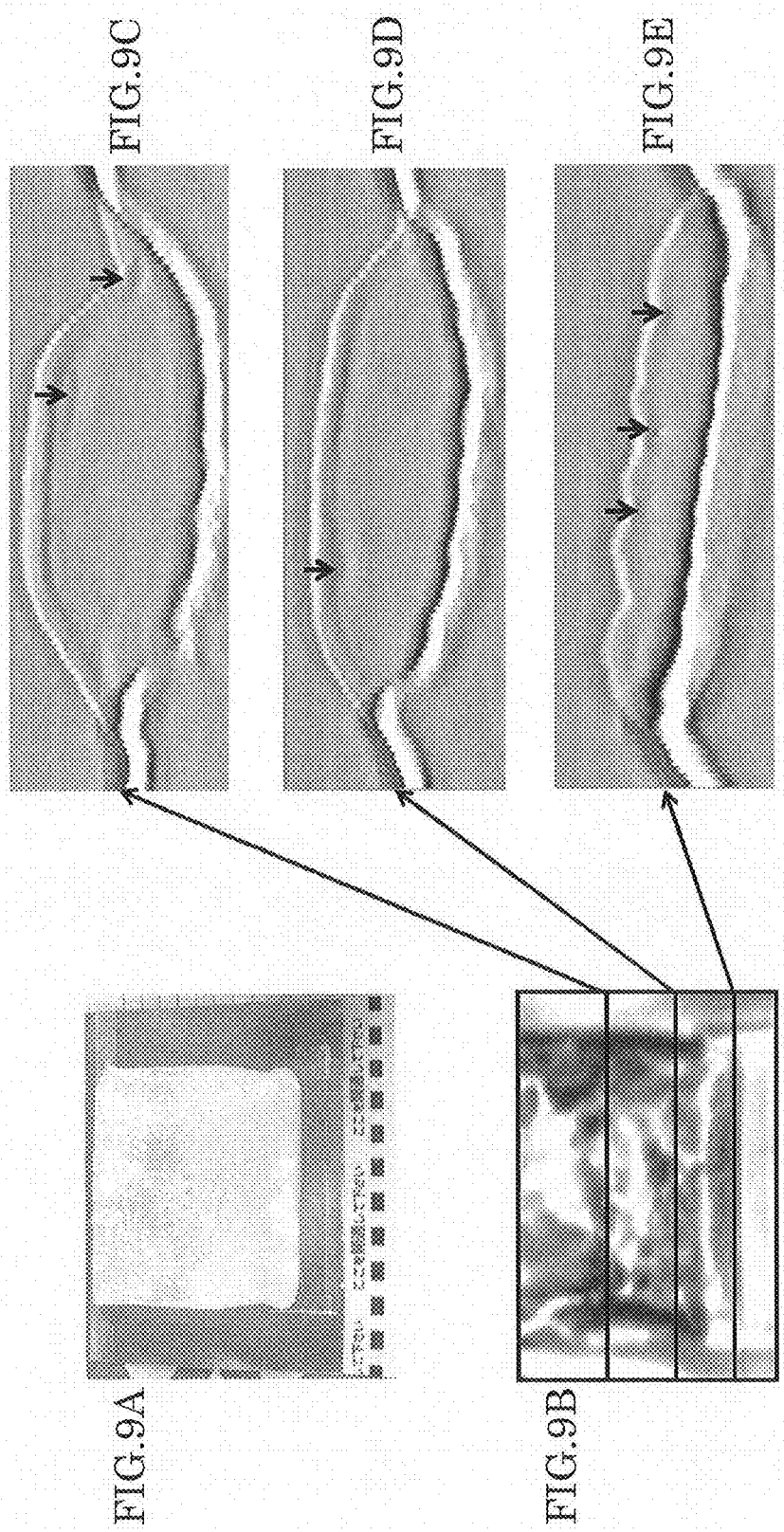

Sample 5    Resin foreign matter 4    Silicone rubber(Si)
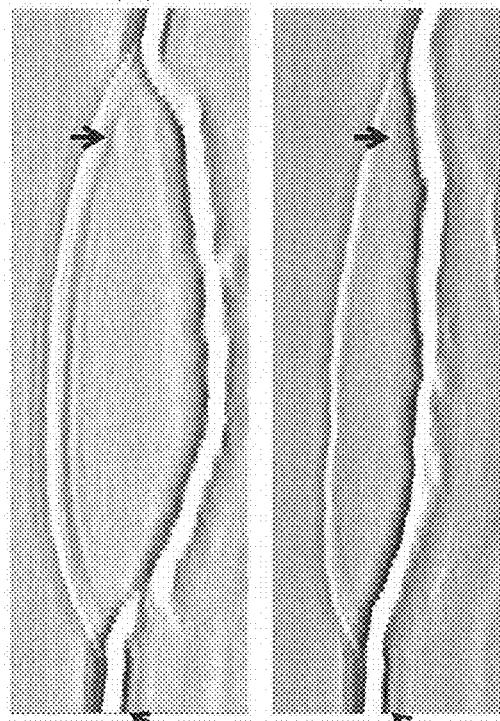
FIG.10A
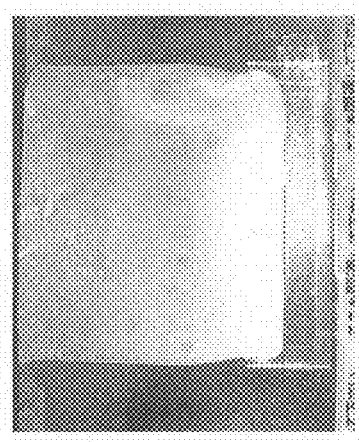
FIG.10B
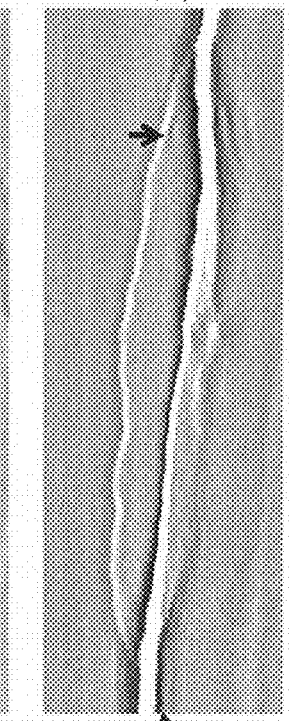
FIG.10C
FIG.10D
FIG.10E
This resin-based foreign matter differs in transmittance of the terahertz wave, ensuring the detection.

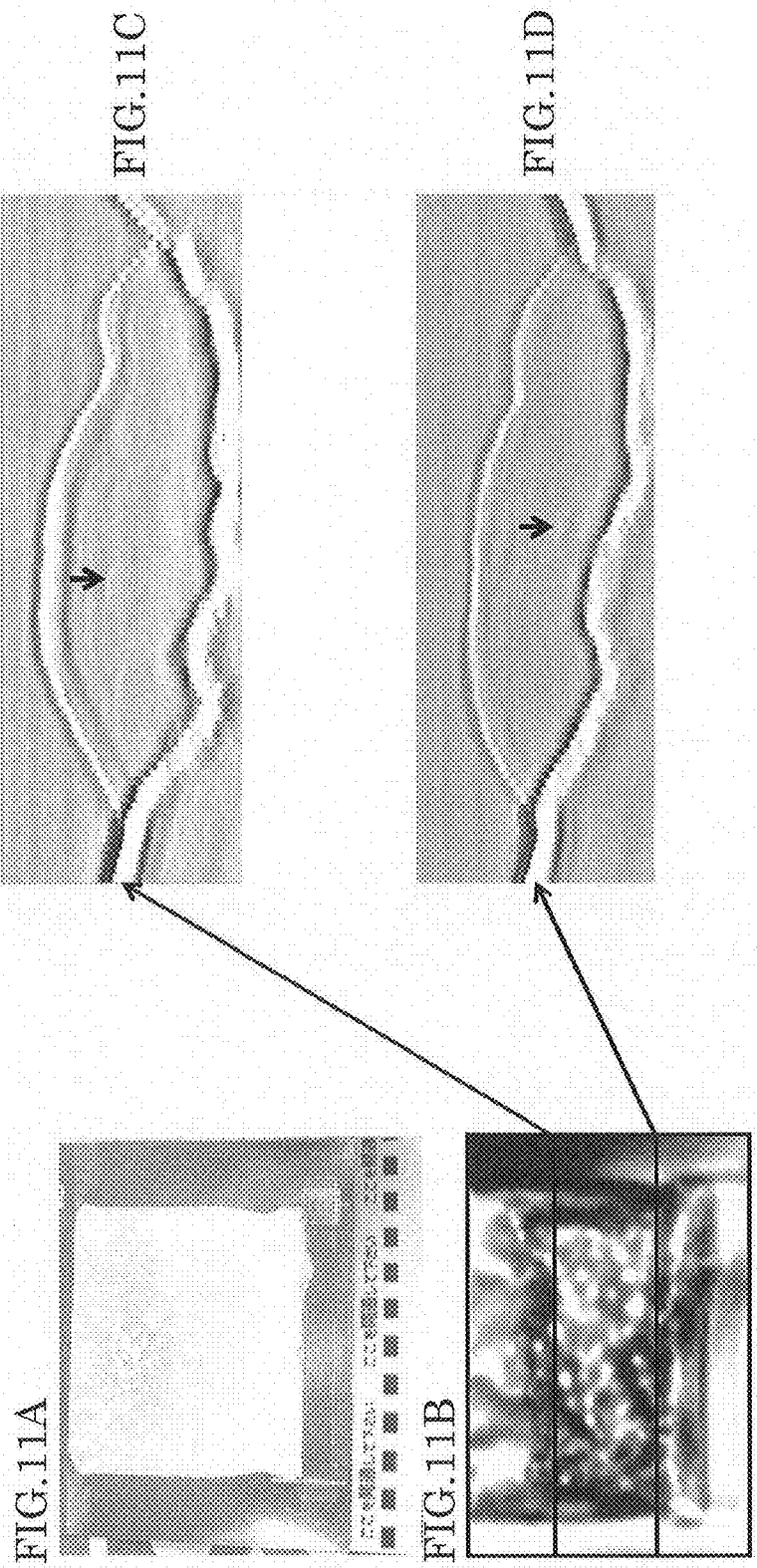

Sample 1 Hair in Lactose
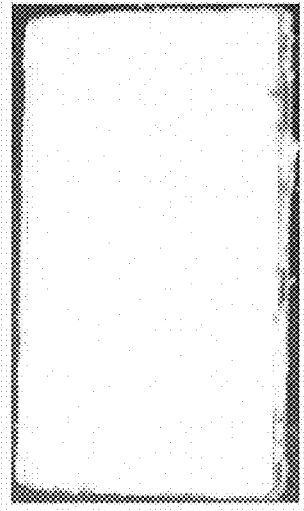
FIG.12A Arrangement of hair
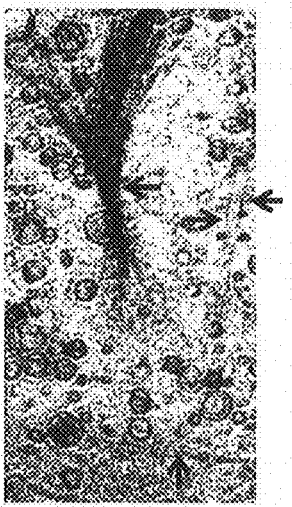
FIG.12B Visible image
(The lactose is covered at thickness of 3 mm.)
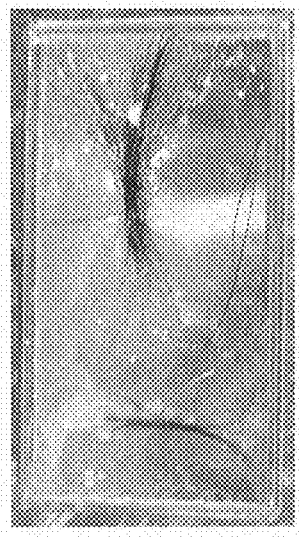
FIG.12C Terahertz wave reflection image
The circular substance is possibly a spherically hardened lactose.
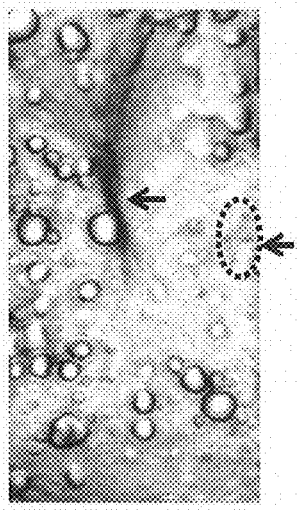
FIG.12D Frequency image (0.62THz)
Each hair can be recognized.

Terahertz tomographic image

A-A'

B-B'

The hair in the lactose can be detected with the terahertz wave reflection image, the tomographic image, and the frequency image.

Example of frequency image
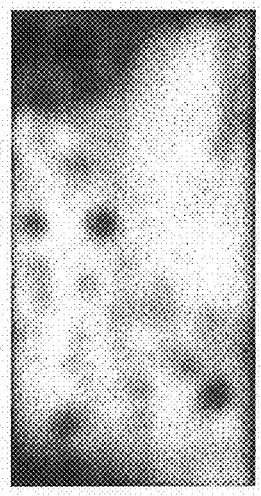
FIG.14A Visible image (Reference)
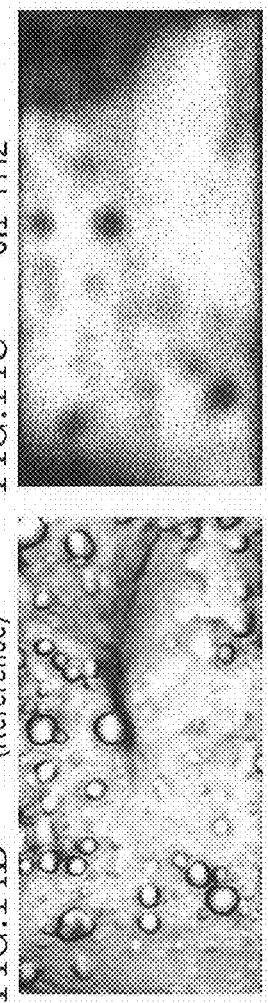
FIG.14B Terahertz wave reflection image (Reference)
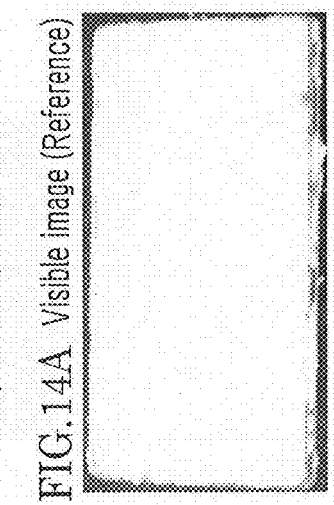
FIG.14D 0.2 THz
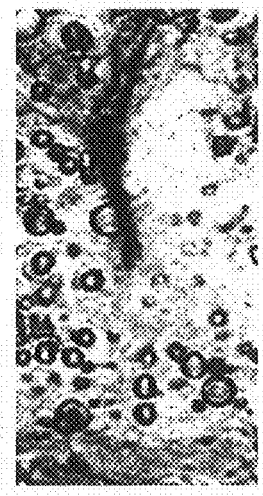
FIG.14C 0.1 THz
FIG.14E 0.31 THz
FIG.14F 0.4 THz
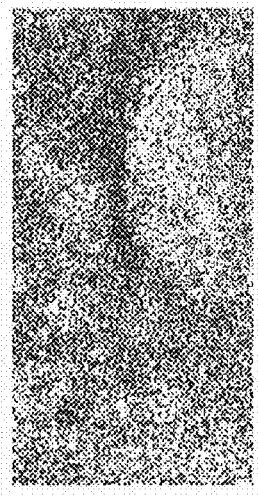
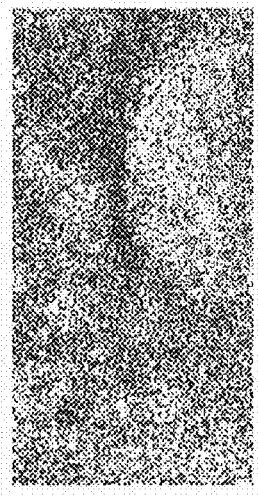
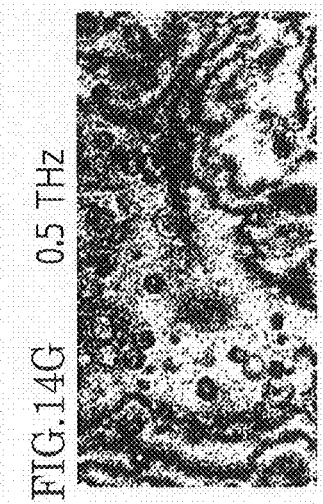
FIG.14G 0.5 THz
FIG.14H 0.62 THz (Optimal value)
FIG.14I 0.8 THz // FOREIGN-MATTER DETECTING APPARATUS AND METHOD FOR DETECTING FOREIGN-MATTER IN POWDER USING TERAHERTZ PULSE WAVE

CROSS-REFERENCE TO RELATED APPLICATIONS

This application claims priority on Japanese Patent Application No. 2012-137127 filed in Japan on Jun. 18, 2012, the entire contents of which are incorporated herein by reference. Moreover, all documents cited in this specification are herein incorporated by reference.

BACKGROUND OF INVENTION

1. Field of Invention

The present invention relates to a foreign-matter detecting apparatus in powder and a method for detecting the foreign matter. In particular, the present invention relates to the foreign-matter detecting apparatus in powder stored in a container made of, for example, a resin sheet, such as polyethylene (PE) and polypropylene (PP), and an aluminum sheet and the method for detecting the foreign matter.

2. Description of Related Art

Conventionally, there is known the following medical container and powder container. The medical container and the powder container have two chambers partitioned by communicable isolation means. One of the two chambers seals an excipient such as glucose and lactose and powder of a medicinal active substance. The other one of the two chambers seals a solution.

Such container can separately store the powder of a medical agent or a similar powder and a solution until immediately before use. Applying external pressure immediately before use brings both chambers into communication with one another. Accordingly, the powder is dissolved into the solution, thus obtaining a liquid medicine.

On a rare occasion, foreign matter is possibly mixed with the powder in such container. For the purpose of use, the foreign matter should never be overlooked. Accordingly, an inspection of foreign matter during manufacture is necessary.

Conventionally, for example, a container is vibrated by a vibrator to cause the foreign matter to float up from the powder by the vibration. Then, an inspector visually checks for the foreign matter. However, visual inspection requires considerable time. Moreover, if a person other than a person with experience performs the visual inspection, the foreign matter can be overlooked. Additionally, foreign matter may not float up from a powder of poor fluidity even after vibration. Accordingly, such visual inspection is unsuitable. An inspection process involving a person like the inspector may be a rate-determining step in production. Therefore, it is desirable for the inspection process to be unmanned and automated.

An inspection apparatus using X-rays can detect metallic foreign matter. However, accurate detection of non-metallic foreign matter such as a resin and a splinter was extremely difficult.

Meanwhile, an analysis technique using an electromagnetic wave in a terahertz range (for example, see Non-Patent Literature 1 and Non-Patent Literature 2) is known. A nondestructive testing device using a terahertz wave or a similar device has already been commercially available.

For example, the following apparatuses and inspection methods have also been proposed. There is provided a foreign matter inspection apparatus in particulate using a sub-terahertz electromagnetic wave and an inspection method (for example, see Patent Literature 1). There is also provided a specimen inspecting apparatus and a specimen inspecting method (for example, see Patent Literature 2) that can reliably detect a heterogeneous medical agent and pharmaceutical ingredient and a substance other than medicines using terahertz time-domain spectroscopy.

The foreign matter inspection apparatus in particulate described in Patent Literature 1 is the foreign matter inspection apparatus in particulate using the sub-terahertz electromagnetic wave. The foreign matter inspection apparatus in particulate includes electromagnetic wave irradiation means, detecting means, signal processing means, and information processing means. The electromagnetic wave irradiation means irradiates a pulsed electromagnetic wave at a wavelength of 600 μm to 3 mm (0.5 THz to 100 GHz) to an object to be inspected. The detecting means detects a space distribution of the transmitted pulsed electromagnetic wave. The signal processing means obtains a difference in transmission time or a difference in amplitude of the pulsed electromagnetic wave due to objects to be inspected. The information processing means indicates the difference in transmission time or the difference in amplitude due to the above-described objects to be inspected.

The specimen inspecting apparatus described in Patent Literature 2 includes a terahertz wave generation unit, an optical system, a detection unit, and a determination unit. The terahertz wave generation unit generates light rays of a terahertz wave. The optical system guides the terahertz wave generated by the terahertz wave generation unit to a sample as an object to be inspected. The detection unit detects a terahertz output wave transmitted through or reflected from the sample as an electrical signal. The determination unit obtains a spectral spectrum from the electrical signal detected by the detection unit. The determination unit then determines whether the sample contains heterogeneous or foreign matter or not based on this spectral spectrum and a predetermined spectral spectrum (fingerprint spectrum) due to a component unique to the sample.

CITATION LIST

Patent Literature

PATENT LITERATURE 1: Japanese Unexamined Patent Application Publication No. 2001-066375
PATENT LITERATURE 2: WO 2008-001785
NON-PATENT LITERATURE 1: Ryoichi FUKASAWA, "Terahertz Time Domain Spectroscopy and Analytical Chemistry", Analysis, The Japan Society for Analytical Chemistry, June 2005, p. 290 to 296
NON-PATENT LITERATURE 2: Ryoichi FUKASAWA, "Analysis of the industrial materials by terahertz sensing", Applied physics, The Spectroscopical Society of Japan, 2010, the 79th volume, the fourth issue, p. 312 to 316

Technical Problem

However, the above-described conventional techniques cannot always and accurately detect all foreign matter other than a metal, such as a resin, a carbonized medical agent, and hair. Especially, whether the foreign matter (in particular, hair) in powder sealed in a medical container, whose casing front surface is made of a resin sheet such as PE and PP and whose casing back surface is made of an aluminum sheet, can be accurately detected or not had not been validated. Further, for example, an optimum condition for detecting the foreign matter was not found.

SUMMARY OF INVENTION

The present invention has been made in view of the above-described problems of the conventional techniques, and it is an object of the present invention to provide a foreign-matter detecting apparatus in powder using a terahertz pulse wave that can accurately detect foreign matter in powder sealed in a medical container whose casing front surface is made of a resin sheet such as PE and PP and whose casing back surface is made of an aluminum sheet and a method for detecting the foreign matter.

Solutions to the Problems

In order to achieve the above object, a foreign-matter detecting apparatus in powder using a terahertz pulse wave according to the present invention is configured to detect foreign matter in powder stored in a container. The container has a first part and a second part. The first part causes most of a terahertz pulse wave to transmit. The second part causes a terahertz pulse wave not to transmit but to reflect the terahertz pulse wave. The foreign-matter detecting apparatus includes an oscillating unit, an optical system, a receiving unit, a scanning mechanism, and an operator. The oscillating unit is configured to generate a terahertz pulse wave and emit the terahertz pulse wave as irradiation light. The optical system is configured to guide the irradiation light emitted from the oscillating unit to the first part of the container and condense reflected light reflected from the container. The receiving unit is configured to output a signal corresponding to the reflected light condensed by the optical system and also measure an echo. The scanning mechanism is configured to scan a position of the irradiation light guided by the optical system on the first part in a two-dimensional manner. The operator is configured to detect (presence/absence, a kind, or a similar state of) foreign matter in the powder in the container based on at least one of a value, a reflection image, a power spectrum, a tomographic image, and a frequency image. The value corresponds to a time waveform signal output from the receiving unit in chronological order. The reflection image has respective pixel values found by time-integrating the time waveform signals. The power spectrum is found by calculating the time waveform signal by Fourier transform. The tomographic image is obtained from a measurement result of the echo. The frequency image has respective pixel values found by calculating the time waveform signal by Fourier transform.

Here, the first part may be made of a resin sheet. The first part may be formed at a first surface side of the container. The second part may be made of an aluminum sheet. The second part may be formed at a second surface side of the container. The second surface side may be disposed at an opposite side of the container from the first surface side. The foreign matter includes, for example, hair as well as metal and resin. However, this should not be construed in a limiting sense.

In the foreign-matter detecting apparatus with this configuration, although the terahertz wave transmits both the first part of the container and the powder sealed in the container, the transmittance to the foreign matter mixed in the powder differs. Accordingly, even if the foreign matter is not only metal or resin but also hair, combining one or more of the time waveform signal, the terahertz wave reflection image, the power spectrum, the tomographic image, and the frequency image allows detection with significant accuracy.

In the foreign-matter detecting apparatus of the present invention, the terahertz pulse wave preferably has a frequency of 1 THz or less.

In the foreign-matter detecting apparatus with this configuration, even if the powder sealed in the container is a medical agent containing a medicinal active substance, the terahertz wave transmittance is sufficiently high. This improves detection accuracy of the foreign matter mixed into such a powder.

Alternatively, a method for detecting foreign matter in powder using a terahertz pulse wave according to the present invention is a method for detecting foreign matter in powder stored in a container. The container has a first part and a second part. The first part causes most of a terahertz pulse wave to transmit. The second part causes a terahertz pulse wave not to transmit but to reflect the terahertz pulse wave. The method for detecting foreign matter includes an oscillating step, a receiving step, a scanning step, and an operation step. The oscillating step generates a terahertz pulse wave and emits the terahertz pulse wave as irradiation light. The receiving step guides the irradiation light emitted at the oscillating step to the first part of the container, condenses reflected light reflected from the container, outputs a signal corresponding to the reflected light thus condensed, and also measures an echo. The scanning step scans a position on the first part where the irradiation light is guided in a two-dimensional manner. The operation step detects (presence/absence, a kind, or a similar state of) foreign matter in the powder in the container based on at least one of a value, a reflection image, a power spectrum, a tomographic image, and a frequency image. The value corresponds to a time waveform signal output at the receiving step in chronological order. The reflection image has respective pixel values found by time-integrating the time waveform signals. The power spectrum is found by calculating the time waveform signal by Fourier transform. The tomographic image is obtained from a measurement result of the echo. The frequency image has respective pixel values found by calculating the time waveform signal by Fourier transform.

In the method for detecting foreign matter with this configuration, although the terahertz wave transmits both the first part of the container and the powder sealed in the container, the transmittance to the foreign matter mixed in the powder differs. Accordingly, even if the foreign matter is not only a metal or a resin but also hair, combining one or more of the time waveform signal, the terahertz wave reflection image, the power spectrum, the tomographic image, and the frequency image allows detection with significant accuracy.

Alternatively, a foreign-matter detecting apparatus according to the present invention is configured to detect foreign matter in powder. The foreign-matter detecting apparatus includes an oscillating unit, an optical system, a receiving unit, a scanning mechanism, and an operator. The oscillating unit is configured to generate a terahertz pulse wave and emit the terahertz pulse wave as irradiation light. The optical system is configured to guide the irradiation light emitted from the oscillating unit to the powder and condense reflected light reflected from the powder and/or transmitted light that has transmitted the powder. The receiving unit is configured to output a signal corresponding to the reflected light and/or the transmitted light condensed by the optical system and also measure an echo. The scanning mechanism is configured to scan a position of the irradiation light guided by the optical system on the powder. The operator is configured to detect foreign matter in the powder based on at least one of a value, a reflection image, a power spectrum, a tomographic image, and a frequency image. The value corresponds to a time waveform signal output from the receiving unit in chronological order. The reflection image has respective pixel values found by time-integrating the time waveform signals. The power spectrum is found by calculating the time waveform signal by Fourier transform. The tomographic image is obtained from a measurement result of the echo. The frequency image has respective pixel values found by calculating the time waveform signal by Fourier transform.

Alternatively, a method for detecting foreign matter according to the present invention is a method for detecting foreign matter in powder. The method for detecting foreign matter includes an oscillating step, a receiving step, a scanning step, and an operation step. The oscillating step generates a terahertz pulse wave and emits the terahertz pulse wave as irradiation light. The receiving step guides the irradiation light emitted at the oscillating step to the powder, condenses reflected light reflected from the powder and/or transmitted light that has transmitted the powder, outputs a signal corresponding to the reflected light and/or the transmitted light thus condensed, and also measures an echo. The scanning step scans a position of the irradiation light guided on the powder. The operation step detects foreign matter in the powder based on at least one of a value, a reflection image, a power spectrum, a tomographic image, and a frequency image. The value corresponds to a time waveform signal output at the receiving step in chronological order. The reflection image has respective pixel values found by time-integrating the time waveform signals. The power spectrum is found by calculating the time waveform signal by Fourier transform. The tomographic image is obtained from a measurement result of the echo. The frequency image has respective pixel values found by calculating the time waveform signal by Fourier transform.

In the foreign-matter detecting apparatus and the method for detecting foreign matter with this configuration, even if the powder is not stored in the container, when the terahertz wave transmits and reflects the powder, the transmittance to the foreign matter mixed in the powder or a similar status differs. Accordingly, even if the foreign matter is not only metal or resin but also hair, combining one or more of the time waveform signal, the reflection image, the power spectrum, the tomographic image, and the frequency image allows detection with significant accuracy.

Advantageous Effects of Invention

In the foreign-matter detecting apparatus in powder and the method for detecting foreign matter using the terahertz pulse wave of the present invention, although the terahertz wave transmits both the first part of the container and the powder sealed in the container, the transmittance at the foreign matter mixed in the powder differs. Accordingly, even if the foreign matter is not only metal or resin but also hair, combining one or more of the time waveform signal, the terahertz wave reflection image, the power spectrum, the tomographic image, and the frequency image allows detection with significant accuracy.

In the case where frequency of the terahertz pulse wave is set to 1 THz or less, even if the powder sealed in the container is a medical agent containing a medicinal active substance such as an antibiotic substance, the detection accuracy of the foreign matter is improved.

BRIEF DESCRIPTION OF THE DRAWINGS

FIG. 8A is a visible image illustrating a medical container that stores powder containing metal foreign matter and a measured area. FIG. 8B is a terahertz wave reflection image. FIG. 8C to FIG. 8G are images exemplifying tomographic images along the respective solid lines in FIG. 8B.

FIG. 9A is a visible image illustrating a medical container that stores powder containing resin foreign matter. FIG. 9B is a terahertz wave reflection image. FIG. 9C to FIG. 9E are images exemplifying tomographic images along the respective solid lines in FIG. 9B.

FIG. 10A is a visible image illustrating a medical container that stores powder containing resin foreign matter. FIG. 10B is a terahertz wave reflection image. FIG. 10C to FIG. 10E are images exemplifying tomographic images along the respective solid lines in FIG. 10B.

FIG. 11A is a visible image illustrating a medical container that stores powder containing a carbonized medical agent. FIG. 11B is a terahertz wave reflection image. FIG. 11C and FIG. 11D are images exemplifying tomographic images along the respective solid lines in FIG. 11B.

FIG. 12A is a visible image illustrating an arrangement of hair. FIG. 12B is a visible image illustrating a state of covering the hair with lactose at a thickness of 3 mm. FIG. 12C is a terahertz wave reflection image. FIG. 12D is an image exemplifying each frequency image (0.62 THz).

FIG. 14A is a visible image that is the same as FIG. 12B. FIG. 14B is a terahertz wave reflection image that is the same as FIG. 12C and FIG. 13A. FIG. 14C to FIG. 14I are images exemplifying respective frequency images obtained by changing a frequency of the terahertz wave in a range of 0.1 to 0.8 THz.

DESCRIPTION OF EMBODIMENTS

Figure 1:
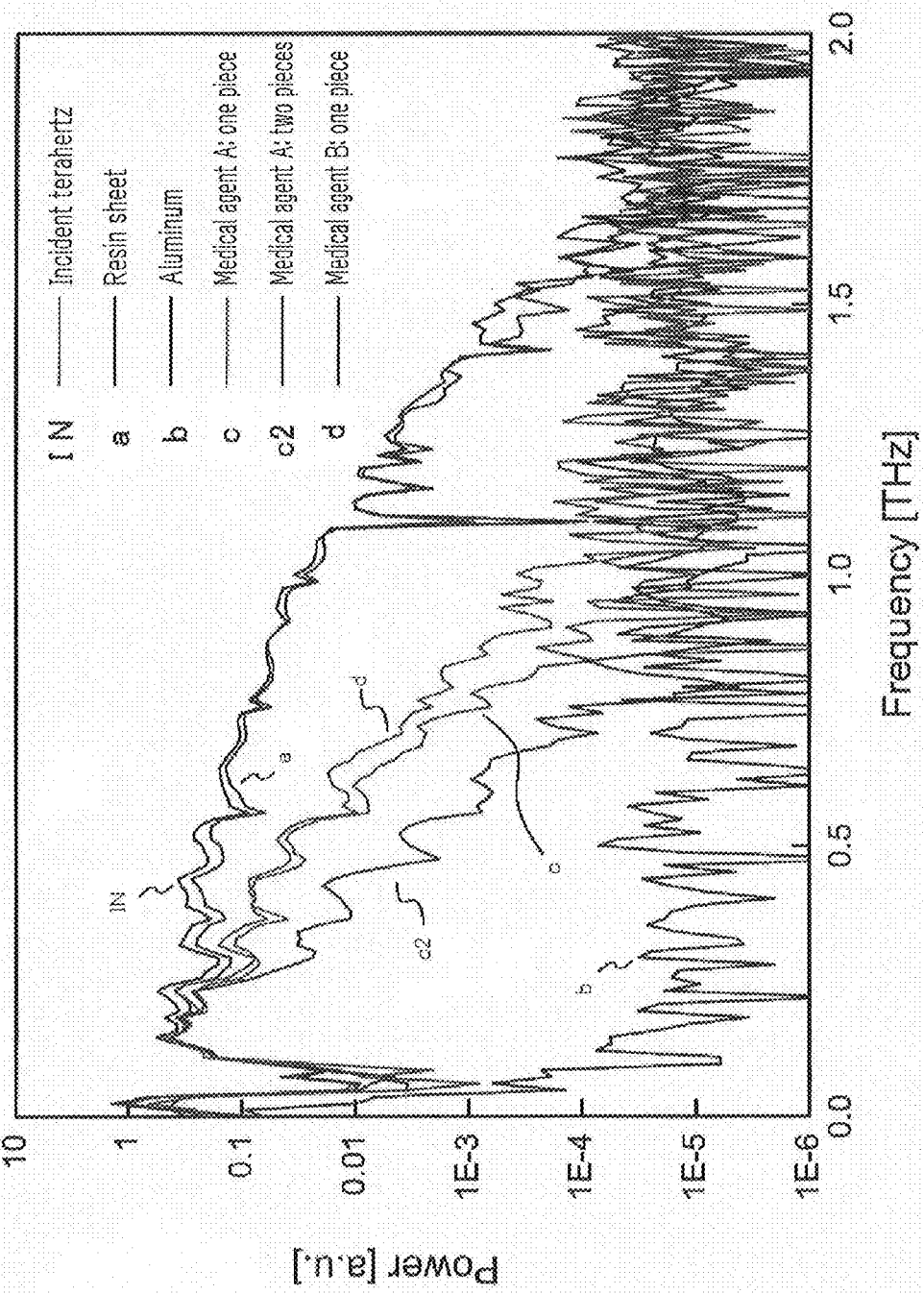
FIG. 1 is a graph showing frequency characteristics of terahertz wave transmittance of, for example, a casing of a medical container 20 and powder sealed in the medical container 20.

Hereinafter, a description will be given of an embodiment of the present invention by referring to the drawings.

<Measured Sample>

First, the following describes a sample measured when detecting foreign matter according to the present invention. As the measured sample, for example, a medical container 20 is available. The medical container 20 has at least two chambers partitioned by communicable isolation means. At least a part of a casing front surface (first surface) is made of a resin sheet (first part) such as PE and PP. A casing back surface (second surface) is made of an aluminum sheet (second part).

One chamber of the medical container 20 seals, for example, glucose, lactose, powder of a medical agent containing a medical active ingredient such as an antibiotic substance, or a similar material. Another chamber seals a solution. Applying external pressure immediately before use brings both chambers into communication. Accordingly, the powder is dissolved into the solution, thus obtaining a liquid medicine.

FIG. 1 is a graph showing frequency characteristics of terahertz wave transmittance of, for example, a casing of the medical container 20 and powder sealed in the medical container 20. Here, a preparation where powder of a medical agent with composition of sulbactam sodium 1 g (potency) and ampicillin sodium 2 g (potency) is sealed in the medical container 20 is referred to as a preparation A. Meanwhile, a preparation where powder of a medical agent with composition of cefepime hydrochloride hydrate 1 g (potency) and L-arginine 0.72 g is sealed in the medical container 20 is referred to as a preparation B.

As shown in this graph, with the resin sheet (a) used for the casing front surface of the medical container 20, an output approximately the same as an incident wave (IN) is obtained. This means that the resin sheet (a) exhibits high permeability across almost the entire region of the measured terahertz band (up to 2 THz).

On the other hand, the aluminum (b) used for the casing back surface of the medical container 20 hardly transmits but reflects the terahertz wave. Additionally, the following is found. The powder of the medical agent such as the preparation A (c and c2) and the preparation B (d) transmits most of a low-frequency component in the terahertz band (approximately 1 THz or less). However, transmittance is gradually degraded as an increase of the frequency.

From these aspects, any one of the low-frequency components in the terahertz band transmits both the casing front surface of the medical container 20 and the sealed powder. It has been found that there is a possibility of ensuring detection of the foreign matter mixed in the powder.

Configuration of Foreign-Matter Detecting Apparatus 10

Figure 2:
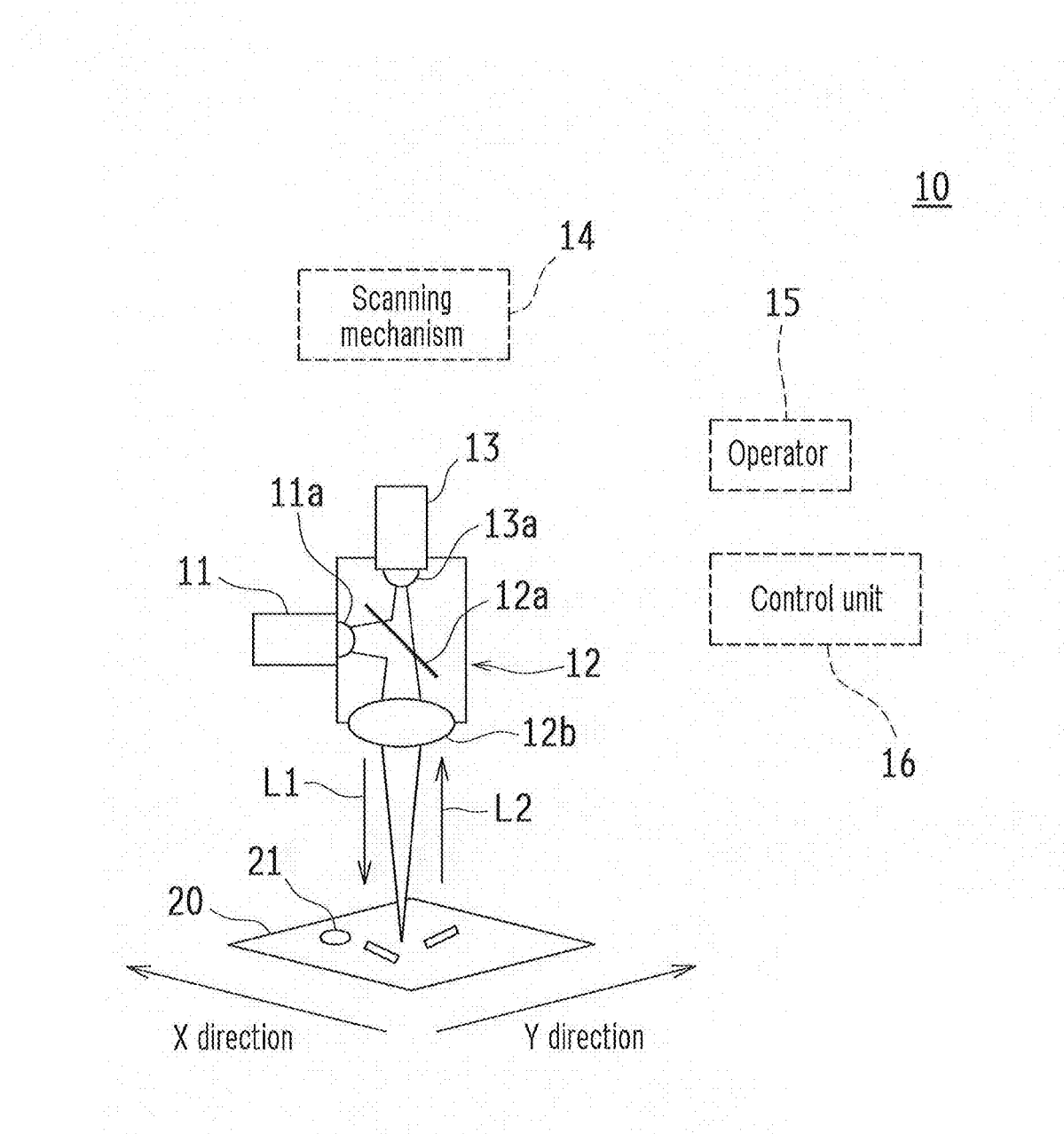
FIG. 2 illustrates an outline of a foreign-matter detecting apparatus 10 according to one embodiment of the present invention.
Figure 3:
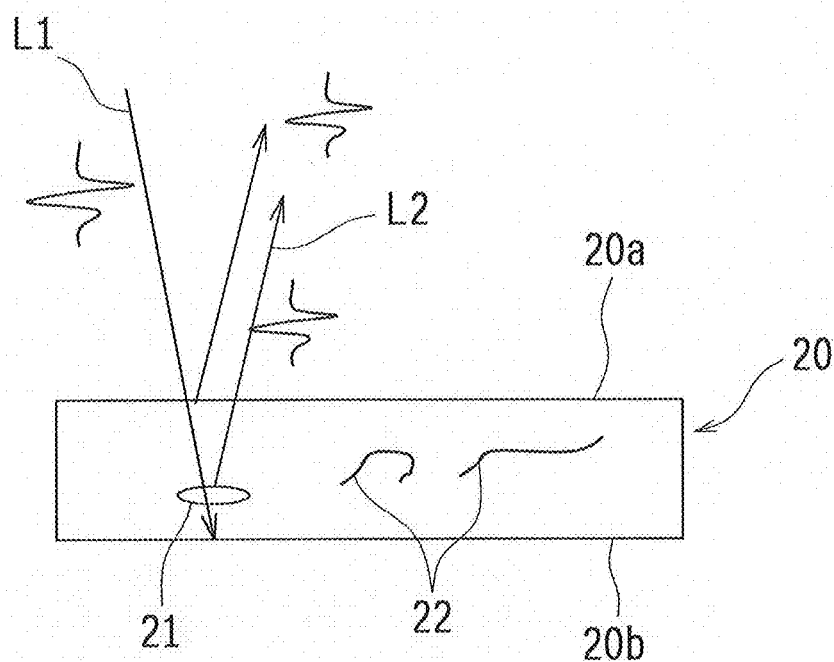
FIG. 3 is a schematic explanatory view illustrating a principle of detecting foreign matter with the foreign-matter detecting apparatus 10.
Figure 4:
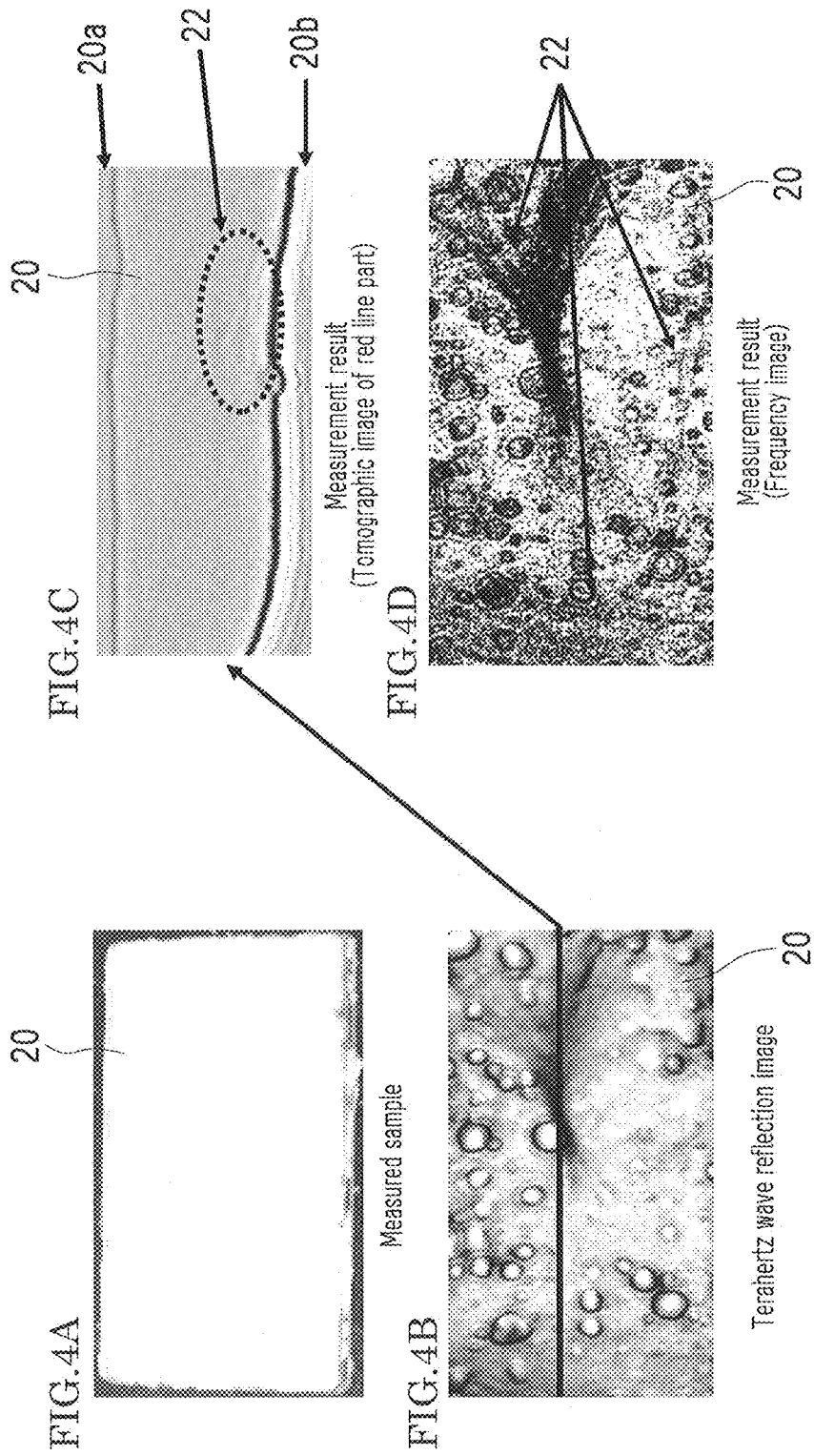
FIG. 4A is a visible image of a measured sample.
FIG. 4B is a terahertz wave reflection image.
FIG. 4C is a tomographic image along the solid line in FIG. 4B.
FIG. 4D is an image exemplifying each frequency image.
Figure 5:
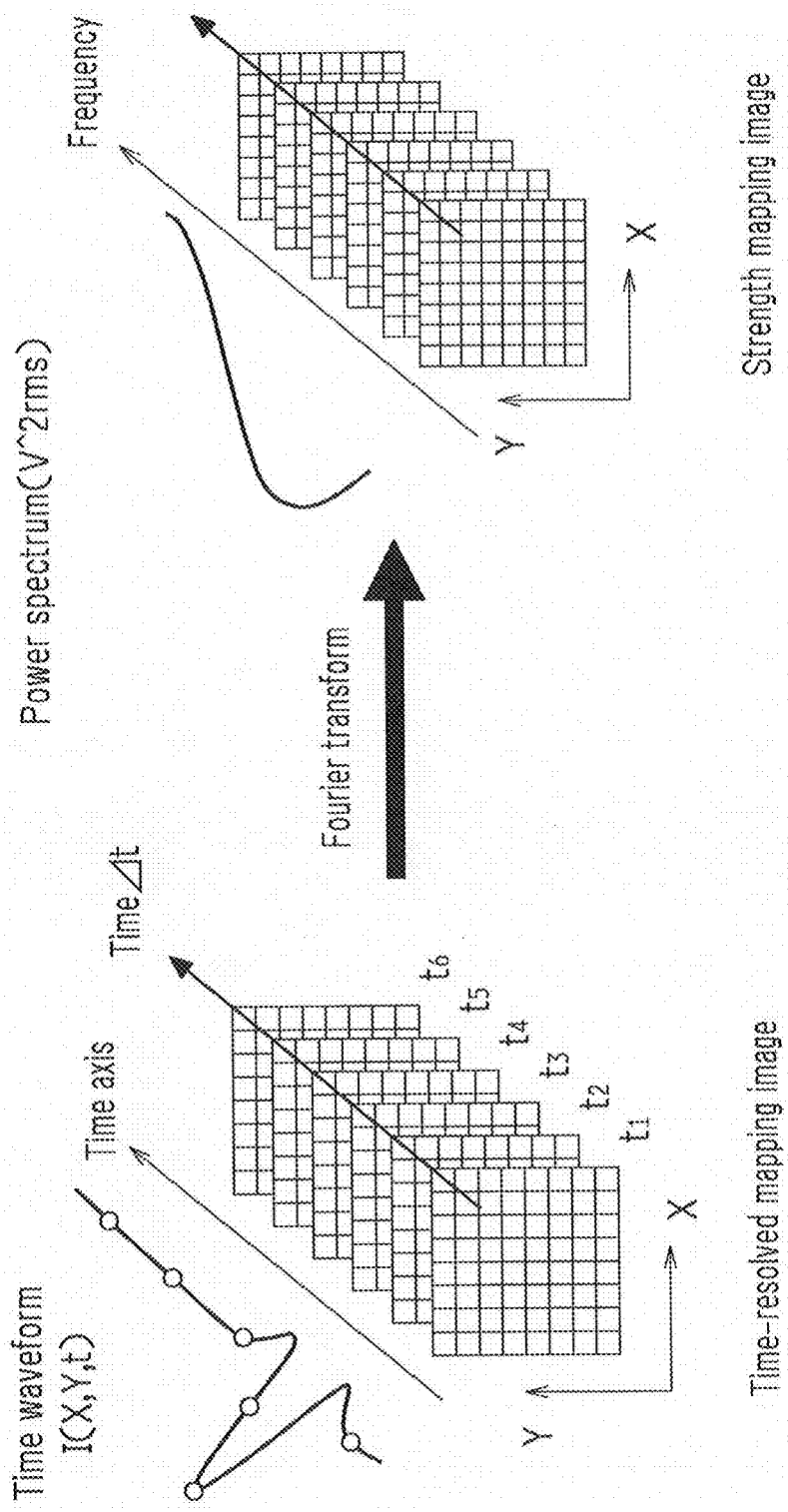
FIG. 5 is an explanatory view illustrating transform processing from a time-resolved mapping image into a strength mapping image by Fourier transform.
Figure 6:
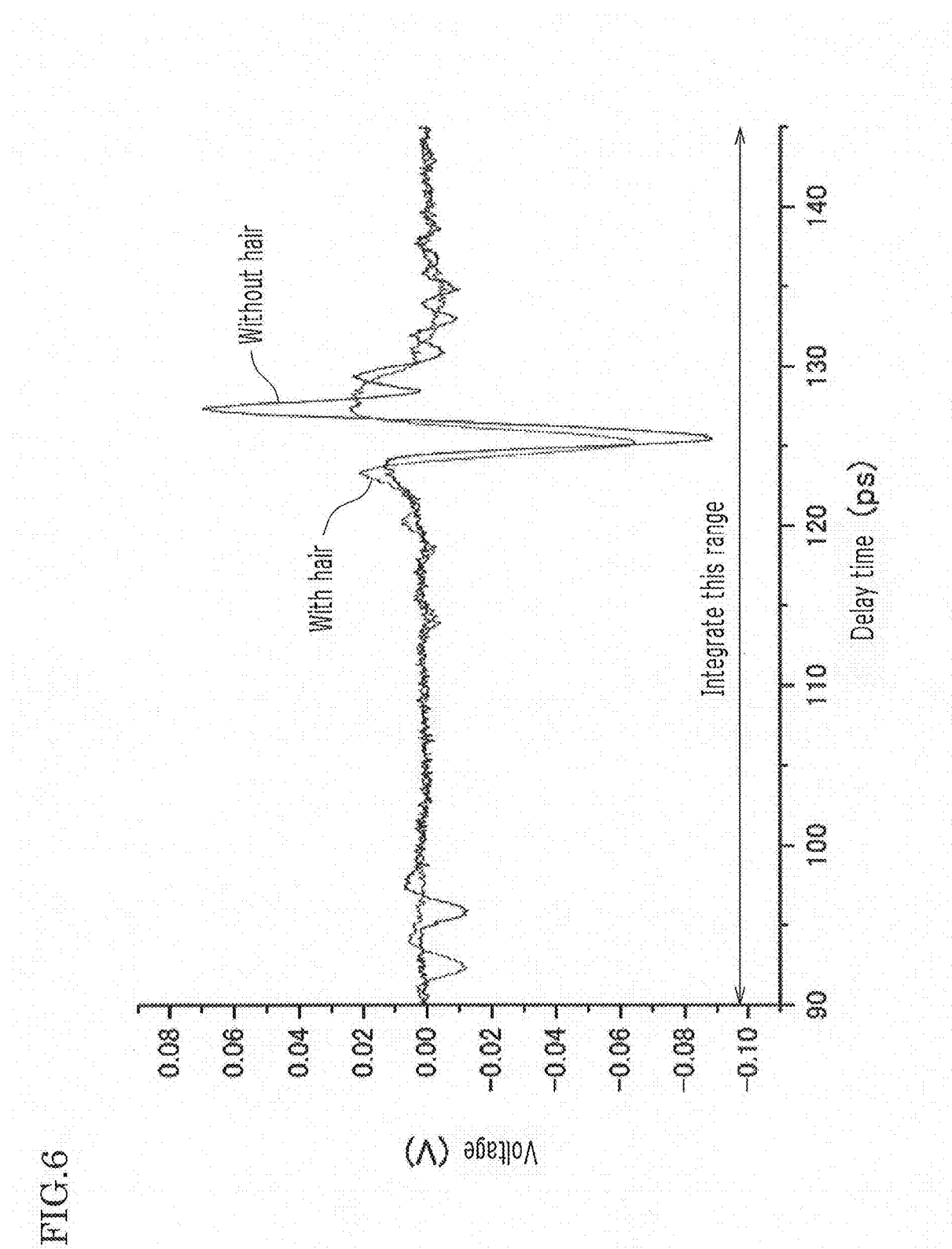
FIG. 6 is a graph exemplifying signals (time waveform signals) output in chronological order.
Figure 7:
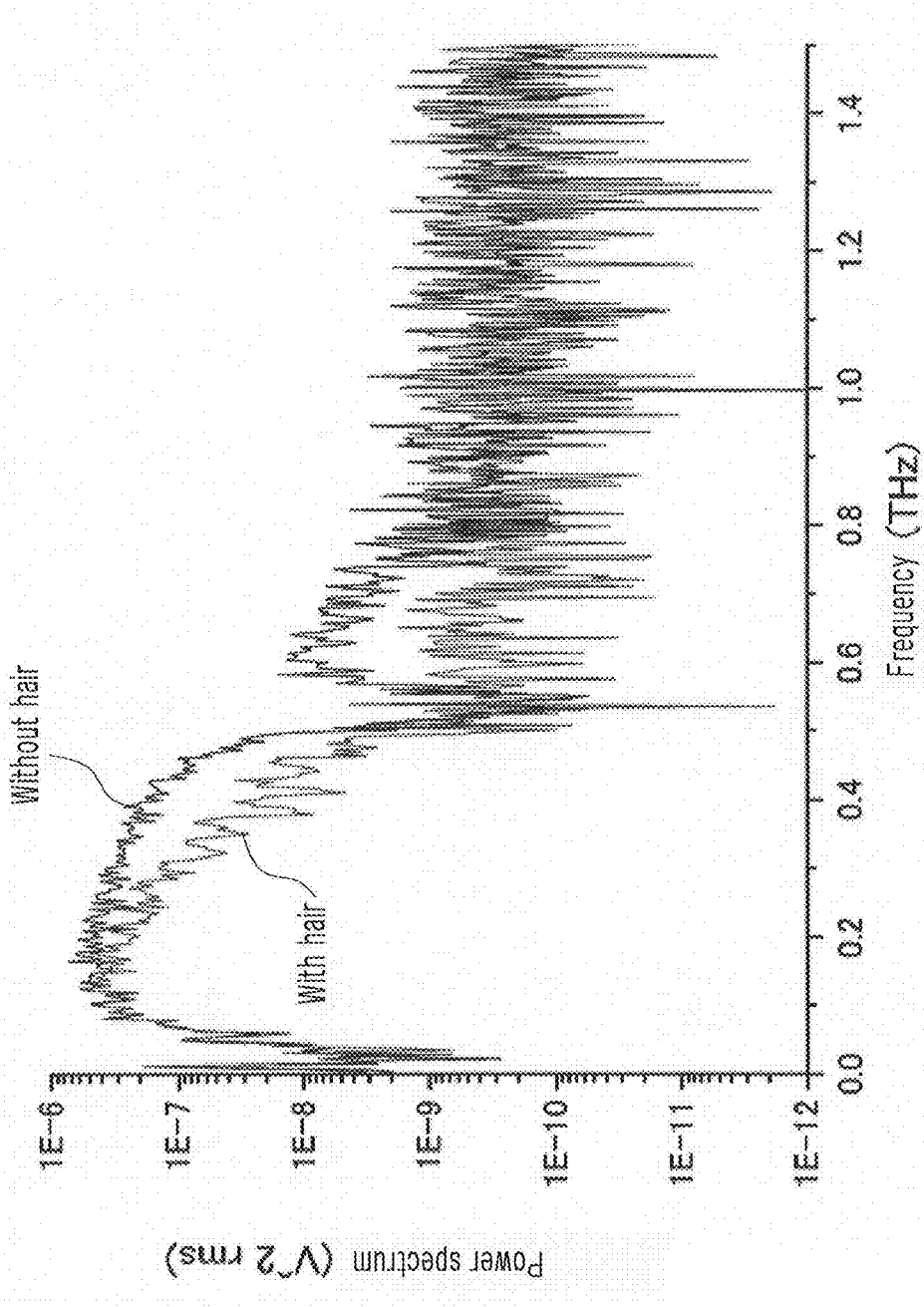
FIG. 7 is a graph exemplifying a power spectrum obtained from the signals (time waveform signals) output in chronological order by Fourier transform.

FIG. 2 illustrates an outline of the foreign-matter detecting apparatus 10 according to one embodiment of the present invention. FIG. 3 is a schematic explanatory view illustrating a principle of detecting foreign matter with the foreign-matter detecting apparatus 10. FIG. 4A is a visible image of a measured sample. FIG. 4B is a terahertz wave reflection image. FIG. 4C is a tomographic image along the solid line in FIG. 4B. FIG. 4D is an image exemplifying each frequency image. FIG. 5 is an explanatory view illustrating transform processing from a time-resolved mapping image into a strength mapping image by Fourier transform. FIG. 6 is a graph exemplifying signals (time waveform signals) output in chronological order. FIG. 7 is a graph exemplifying a power spectrum obtained from the signal (time waveform signal) output in chronological order by Fourier transform.

As illustrated in FIG. 2, this foreign-matter detecting apparatus 10 includes an oscillator 11, an optical system 12, a receiver 13, a scanning mechanism 14 (The detailed configuration and a similar configuration are not illustrated), an operator 15, and a control unit 16. The oscillator 11 generates the terahertz pulse wave. The optical system 12 guides irradiation light L1 of the terahertz pulse wave, which is generated from the oscillator 11, to a top surface of the measured sample, such as the medical container 20. The optical system 12 also condenses reflected light L2 reflected by the measured sample. The receiver 13 outputs an electrical signal corresponding to the reflected light L2, which is condensed by the optical system 12. The scanning mechanism 14 scans a position of the top surface of the measured sample to which the irradiation light L1 of the terahertz pulse wave is guided by the optical system 12 in a two-dimensional manner. The operator 15 detects, for example, a presence/absence and a kind of foreign matter 21 in the powder sealed in the medical container 20 based on at least one of a reflection image, a tomographic image, and a frequency image obtained from the electrical signal output from the receiver 13. The control unit 16 controls the entire oscillator 11, receiver 13, scanning mechanism 14, operator 15, and a similar unit.

The oscillator 11 generates the terahertz pulse wave including a frequency at 0.1 to 10 THz. The oscillator 11 also refracts the terahertz pulse wave at a hemispherical lens 11a. The hemispherical lens 11a is disposed in the direction of generating the terahertz pulse wave.

The optical system 12 includes a half mirror 12a, a convex lens 12b, or a similar component. The half mirror 12a reflects the terahertz pulse wave, which is generated from the oscillator 11 and refracted by the hemispherical lens 11a, and changes the direction of the terahertz pulse wave to downward. The convex lens 12b guides the irradiation light L1 formed by condensing the terahertz pulse wave whose direction has been changed by the half mirror 12a to the measured sample. The convex lens 12b also refracts reflected light L2 from the measured sample.

Here, as illustrated in FIG. 3, the irradiation light L1 from the oscillator 11 transmits the resin sheet forming a front surface 20a of the medical container 20 almost intact (a part of the irradiation light L1 reflects slightly and becomes a part of the reflected light L2). The transmitted irradiation light L1 is partially reflected by the front surface of the foreign matter 21 (the reflected light later transmits the front surface 20a and becomes a part of the reflected light L2). Another part of the irradiation light L1 is absorbed by the foreign matter 21. The remainder is diffracted by the foreign matter 21 and then transmits the foreign matter 21. The remaining irradiation light L1 thus transmitted is reflected by the aluminum sheet forming a back surface 20b of the medical container 20. Further, the remaining irradiation light L1 transmits the foreign matter 21 again. Then, the remaining irradiation light L1 also transmits the front surface 20a, thus being a part of the reflected light L2.

The receiver 13 condenses the reflected light L2, which has been refracted by the convex lens 12b and has transmitted the half mirror 12a, by a hemispherical lens 13a. The hemispherical lens 13a is disposed at the arrival direction of the reflected light L2. The receiver 13 then outputs the electrical signal corresponding to the strength of the condensed reflected light L2.

The scanning mechanism 14 moves the entire oscillator 11, optical system 12, and receiver 13 in an X direction and a Y direction, which are perpendicular along a plane where the measured sample is placed, while securing the position of the measured sample. This allows the scanning of the measured sample in a two-dimensional manner. However, the entire oscillator 11, optical system 12, and receiver 13 do not need to be moved. Inversely, while securing the respective entire positions of the oscillator 11, the optical system 12, and the receiver 13, the measured sample may be moved in the X direction and the Y direction.

Instead of such movement, when the scanning is performed by periodical driving by at least a part of the optical system 12 (for example, swinging the mirror), scanning at a higher speed can be achieved. In this case, the use of a telecentric optical system is preferable.

For example, a range of the measured sample where the powder of, for example, the medical agent is present is scanned at an interval of 1 mm or less in a two-dimensional manner. At the same time, the electrical signal from the receiver 13 corresponding to the reflected light L2 is obtained in chronological order.

The operator 15 obtains a terahertz wave reflection image (for example, see FIG. 4B). The terahertz wave reflection image has respective pixel values found by time-integrating absolute values of the electrical signals (time waveform signals, for example, see FIG. 6), which are obtained from the receiver 13 in chronological order during two-dimensional scanning by the scanning mechanism 14.

An echo of the terahertz pulse wave is also measured. This allows calculating the tomographic image (for example, see FIG. 4C) along the straight line connecting any given two points at end portions of the reflection image as necessary.

Furthermore, a Fourier transform is performed on time images obtained in chronological order at an interval of a period required for the two-dimensional scanning, namely, time-resolved mapping images (time waveform: I (X, Y, t)). Thus, a power spectrum (for example, see FIG. 7) is obtained as well as the strength mapping image. From this strength mapping image, any given frequency image (for example, see FIG. 4D) can be extracted.

Then, at least one or more of the time waveform signal (value corresponding to the time waveform signal), the reflection image, the power spectrum, the tomographic image, and the frequency image thus obtained are combined appropriately as necessary. This allows detecting the foreign matter contained in the powder in the medical container 20.

<Example of Measurement Image>

(1) Metal Foreign Matter

FIG. 8A is a visible image illustrating a medical container that stores powder containing this metal foreign matter and a measured area. FIG. 8B is a terahertz wave reflection image. FIG. 8C to FIG. 8G are images exemplifying tomographic images along the respective solid lines in FIG. 8B.

As illustrated in these images, this metal foreign matter reflects the terahertz wave. This allows detection by the foreign-matter detecting apparatus 10.

(2) Resin Foreign Matter: Polystyrene

FIG. 9A is a visible image illustrating a medical container that stores powder containing this resin foreign matter. FIG. 9B is a terahertz wave reflection image. FIG. 9C to FIG. 9E are images exemplifying tomographic images along the respective solid lines in FIG. 9B.

As illustrated in these images, this resin foreign matter differs in transmittance of the terahertz wave from the medical container and the powder. This allows detection by the foreign-matter detecting apparatus 10.

(3) Resin Foreign Matter: Silicone Rubber

FIG. 10A is a visible image illustrating a medical container that stores powder containing this resin foreign matter. FIG. 10B is a terahertz wave reflection image. FIG. 10C to FIG. 10E are images exemplifying tomographic images along the respective solid lines in FIG. 10B.

As illustrated in these images, this resin foreign matter differs in transmittance of the terahertz wave from the medical container and the powder. This allows detection by the foreign-matter detecting apparatus 10.

(4) Carbonized Medical Agent

FIG. 11A is a visible image illustrating a medical container that stores powder containing this carbonized medical agent. FIG. 11B is a terahertz wave reflection image. FIG. 11C and FIG. 11D are images exemplifying tomographic images along the respective solid lines in FIG. 11B.

As illustrated in these images, this carbonized medical agent differs in transmittance of the terahertz wave from the medical container and the powder. This allows detection by the foreign-matter detecting apparatus 10.

(5) Hair in Lactose

FIG. 12A is a visible image illustrating an arrangement of hair. FIG. 12B is a visible image illustrating a state of covering the hair with lactose at a thickness of 3 mm. FIG. 12C is a terahertz wave reflection image. FIG. 12D is an image exemplifying each frequency image (0.62 THz).

Figure 13A:
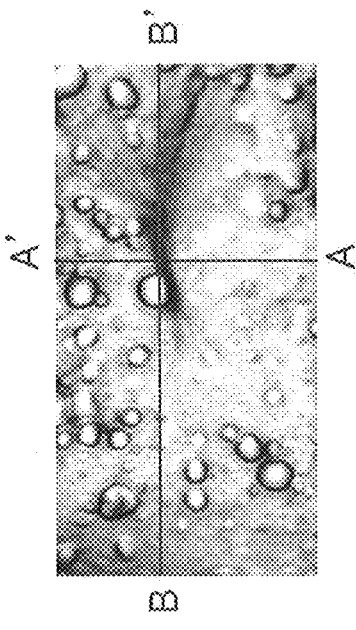
FIG. 13A is a terahertz wave reflection image that is the same as FIG. 12C.
Figure 13B:
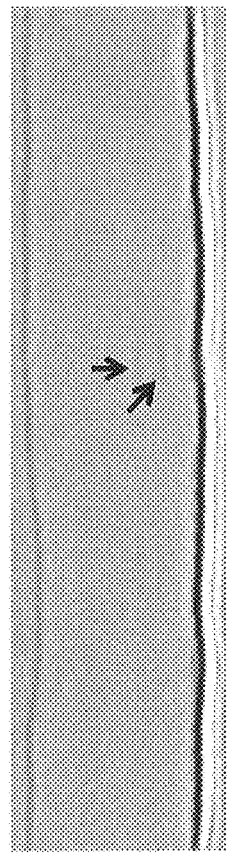
FIG. 13B is an image exemplifying a tomographic image taken along the line A-A' of FIG. 13A.
Figure 13C:
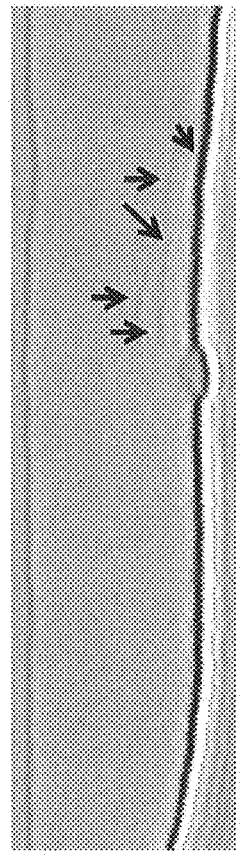
FIG. 13C is an image exemplifying a tomographic image taken along the line B-B' of FIG. 13A.

FIG. 13A is a terahertz wave reflection image that is the same as FIG. 12C. FIG. 13B is an image exemplifying a tomographic image taken along the line A-A' of FIG. 13A. FIG. 13C is an image exemplifying a tomographic image taken along the line B-B' of FIG. 13A.

FIG. 14A is a visible image that is the same as FIG. 12B. FIG. 14B is a terahertz wave reflection image that is the same as FIG. 12C and FIG. 13A. FIG. 13C to FIG. 13I are images exemplifying respective frequency images obtained by changing a frequency of the terahertz wave in a range of 0.1 to 0.8 THz.

As illustrated in these images, in the visible image of FIG. 12B, the hair covered with the lactose naturally cannot be seen. However, in the terahertz wave reflection image of FIG. 12C, a certain extent of the hair (ahead of the arrow) can be visually perceived. The circular substance enclosed by the dashed line is possibly a spherically hardened lactose. The frequency image of FIG. 12D is a result of selecting FIG. 14H where the hair probably can be seen most vividly among FIG. 14C to FIG. 14I. Here, each hair can be recognized.

Thus, the hair in the lactose can be detected based on the terahertz wave reflection image, the tomographic image, and the frequency image. The optimal value of the frequency of terahertz wave in this case is 0.62 THz.

The above-described configuration of this embodiment achieves the following. Even if the foreign matter 21 in the powder of, for example, the lactose sealed in the medical container 20 is not only a metal or a resin but also hair, combining one or more of the time waveform signal, the terahertz wave reflection image, the tomographic image, the power spectrum, and the frequency image where the frequency is appropriately set allows detection with significant accuracy.

<Other Embodiments>

The above-described embodiment describes the foreign-matter detecting apparatus 10 suitable for detection of the foreign matter contained in the powder in the medical container 20. However, the present invention should not be construed in a limiting sense. For example, even if the powder possibly containing the foreign matter is not stored in various medical containers, the terahertz pulse wave may be irradiated to the powder and any one or both of transmitted light that has transmitted the powder and reflected light that has reflected from the powder may be used.

Then, combining one or more of the time waveform signal, the terahertz wave reflection image, the tomographic image, the power spectrum, and the frequency image where the frequency is appropriately set allows similar detection of the foreign matter contained in the powder.

The present invention may be embodied in various other forms without departing from the spirit and scope or essential characteristics thereof. Therefore, the above-described embodiments are to be considered in all respects as illustrative and not limiting. The scope of the invention is indicated by the appended claims rather than by the foregoing description. All modifications or changes that come within the meaning and range of equivalency of the claims are intended to be embraced therein.

DESCRIPTION OF REFERENCE SIGNS 10 foreign-matter detecting apparatus
11 oscillator
11a hemispherical lens
12 optical system
12a half mirror
12b convex lens
13 receiver
13a hemispherical lens
14 scanning mechanism
15 operator
16 control unit
20 medical container
20a front surface
20b back surface
21 foreign matter
22 hair
L1 irradiation light
L2 reflected light

The invention claimed is:

1. A foreign-matter detecting apparatus for detecting foreign matter in powder stored in a container, the container having a first part causing most of a terahertz pulse wave to transmit and a second part causing the terahertz pulse wave not to transmit but to reflect, the foreign-matter detecting apparatus comprising:
   an oscillating unit configured to generate the terahertz pulse wave and emit the terahertz pulse wave as irradiation light;
   a telecentric optical system configured to guide the irradiation light emitted from the oscillating unit to the first part and condense reflected light reflected from the container;
   a receiving unit configured to output a signal corresponding to the reflected light condensed by the telecentric optical system and also measure an echo;
   a scanning mechanism configured to scan a position of the irradiation light guided by the telecentric optical system on the first part in a two-dimensional manner; and
   an operator configured to detect the foreign matter in the powder in the container based on at least one of a value corresponding to a time waveform signal output from the receiving unit in chronological order, a reflection image having respective pixel values found by time-integrating the time waveform signals, a power spectrum being found by calculating the time waveform signal by Fourier transform, a tomographic image being obtained from a measurement result of the echo, and a frequency image having respective pixel values found by calculating the time waveform signal by Fourier transform,
   wherein the telecentric optical system includes a half mirror configured to change a direction of either: (i) the irradiation light emitted from the oscillating unit or (ii) the reflected light to be received by the receiving unit, and
   wherein the scanning is performed by periodical driving by only a part of the telecentric optical system.

2. The foreign-matter detecting apparatus according to claim 1, wherein:
   the first part is made of a resin sheet, the first part being at a first surface side of the container, and
   the second part is made of an aluminum sheet, the second part being at a second surface side of the container, and the second surface side being at an opposite side of the container from the first surface side.

3. The foreign-matter detecting apparatus according to claim 2, wherein
   the terahertz pulse wave has a frequency of 1 THz or less.

4. The foreign-matter detecting apparatus according to claim 3, wherein
   the foreign matter is hair.

5. The foreign-matter detecting apparatus according to claim 2, wherein
   the foreign matter is hair.

6. The foreign-matter detecting apparatus according to claim 1, wherein
   the terahertz pulse wave has a frequency of 1 THz or less.

7. The foreign-matter detecting apparatus according to claim 6, wherein
   the foreign matter is hair.

8. The foreign-matter detecting apparatus according to claim 1, wherein
   the foreign matter is hair.

9. The foreign-matter detecting apparatus according to claim 1, wherein the operator is configured to detect the foreign matter in the powder in the container based on at least two of the value corresponding to the time waveform signal output from the receiving unit in chronological order, the reflection image having respective pixel values found by time-integrating the time waveform signals, the power spectrum being found by calculating the time waveform signal by Fourier transform, the tomographic image being obtained from the measurement result of the echo, and the frequency image having respective pixel values found by calculating the time waveform signal by Fourier transform.

10. The foreign-matter detecting apparatus according to claim 1, wherein the periodical driving includes swinging the half mirror.

* * * * *